US012721924B2

(12) United States Patent
Kuempel et al.

(10) Patent No.: US 12,721,924 B2
(45) Date of Patent: Sep. 1, 2026

(54) DIRECTIONAL ULTRAVIOLET DISINFECTION APPARATUS

(71) Applicant: R-Zero Systems, Inc., S. Salt Lake, UT (US)

(72) Inventors: Jeremy Kuempel, San Francisco, CA (US); Thomas Carlson, Salt Lake City, UT (US); Sivan Sud, Greenwich, CT (US); Wiley Wang, Salt Lake City, UT (US); Neil Day, Portola Valley, CA (US); Ashley Lynn Miller, Santa Barbara, CA (US); John Cody Semones, Cottonwood Heights, UT (US)

(73) Assignee: R-Zero Systems, Inc., San Francisco, CA (US)

(*) Notice: Subject to any disclaimer, the term of this patent is extended or adjusted under 35 U.S.C. 154(b) by 1031 days.

(21) Appl. No.: 17/833,694

(22) Filed: Jun. 6, 2022

(65) Prior Publication Data

US 2022/0387656 A1 Dec. 8, 2022

Related U.S. Application Data

(60) Provisional application No. 63/197,956, filed on Jun. 7, 2021.

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01)

(58) Field of Classification Search
CPC ......................................................... A61L 9/20
See application file for complete search history.

(56) References Cited

U.S. PATENT DOCUMENTS 11,167,057 B1 11/2021 Shalvi
2019/0111169 A1* 4/2019 Flaherty .................. G06F 3/016
(Continued)

FOREIGN PATENT DOCUMENTS

CN 209262813 U 8/2019
CN 210462655 U 5/2020
(Continued)

OTHER PUBLICATIONS

"UV LED to disinfect your water", UV LED disinfecting lighting Philips Lighting, Mar. 23, 2022, 3 pages, https://www.lighting.philips.com/main/products/uv-disinfection/uv-led, 2018-2022 Signify Holding.

(Continued)

*Primary Examiner* — Kevin Joyner

(57) ABSTRACT

An apparatus for disinfecting an air space is presented. The apparatus includes a housing having a front surface, a back surface, a top surface, a bottom surface, a first end, and a second end. A light emitting diode is inside the housing and configured to emit ultraviolet radiation, at least 90% of which has a wavelength less than 280 nm, in a direction away from the housing into surrounding space. Circuits inside the housing control the light emitting diode to emit radiation at different intensity levels including zero. Motion sensors may be coupled to the circuits to turn the light emitting diode on and off and modulate the intensity of radiation that is emitted, thereby avoiding exposing occupants of the space to harmful radiation.

15 Claims, 13 Drawing Sheets

(56) References Cited

U.S. PATENT DOCUMENTS

| | | | | |
|---|---|---|---|---|
| 2020/0197550 | A1* | 6/2020 | Barron | H05K 7/20154 |
| 2021/0178008 | A1 | 6/2021 | Zarcone et al. | |
| 2021/0299317 | A1* | 9/2021 | Mullen | F24F 8/22 |
| 2021/0317981 | A1 | 10/2021 | Higgins et al. | |
| 2021/0330836 | A1 | 10/2021 | Lane | |
| 2021/0364178 | A1 | 11/2021 | Kiviat | |
| 2022/0040363 | A1 | 2/2022 | Ling | |
| 2023/0039310 | A1* | 2/2023 | Baarman | A61L 9/20 |

FOREIGN PATENT DOCUMENTS

| | | | |
|---|---|---|---|
| CN | 111536612 | A | 8/2020 |
| CN | 112843319 | A | 5/2021 |
| DE | 202021103900 | U1 | 7/2021 |
| KR | 10-0998473 | B1 | 12/2010 |
| WO | 2016105347 | A1 | 6/2016 |
| WO | 2022025509 | A1 | 2/2022 |

OTHER PUBLICATIONS

Targus, UV-C LED Disinfection Light Automatically Disinfect High-Touch Surfaces.

International Search Report Corresponding to International application No. PCT/US2022/032393 dated Oct. 7, 2022, 12 pages.

* cited by examiner 10
20
22
22
22
22
24

10
24
openings / holes
50

DIRECTIONAL ULTRAVIOLET DISINFECTION APPARATUS

CROSS-REFERENCE TO RELATED APPLICATION(S)

This application claims the benefit of U.S. Provisional Patent Application No. 63/197,956 filed on Jun. 7, 2021, the content of which is incorporated by reference herein.

BACKGROUND

UV-C radiation has been known to kill or deactivate bacteria, viruses, and other pathogens effectively.

UV-C has been used for disinfection of water, small surfaces, and air space. Disinfection of air space typically involves lamp systems that emit light in the UV-C (100-290 nm) range. These lamp systems typically use low-pressure mercury vapor lamps and are designed to be installed or placed in a room. Disinfection of air space in a room reduces transmission of airborne infectious diseases, especially in high-occupancy settings such as jails, homeless shelters, and hospital emergency rooms. Laboratory tests have shown that UV exposure reduces the average concentration of culturable airborne bacteria, viruses, and pathogens significantly, in some cases by more than half. This type of air space disinfection is proven to be useful against pathogens that are transmitted by the airborne route and cause diseases, such as tuberculosis or COVID-19.

A problem with the UV-C disinfection apparatus is that UV-C may be harmful to humans when exposure exceeds a threshold level. To prevent the UV-C radiation emitted by the mercury lamp from spreading, multiple baffles are used in UV-C disinfection products. Unfortunately, the baffles make the product bulky and often unappealing. Furthermore, monitoring is required to make sure that humans do not enter the disinfection zone while the UV-C radiation is on. A low-maintenance, nonintrusive way of achieving the UV-C disinfection in the background without exposing humans to health risks is desired.

SUMMARY

In one aspect, the disclosure pertains to an apparatus for disinfecting an air space. The apparatus includes a housing having a front surface, a back surface, a top surface, a bottom surface, a first end, and a second end. A light emitting diode is inside the housing and configured to emit ultraviolet radiation, at least 90% of which has a wavelength less than 280 nm, in a direction away from the housing into surrounding space. Circuits inside the housing control the light emitting diode to emit radiation at different intensity levels including zero, thereby avoiding exposing occupants of the room to harmful radiation.

In another aspect, the disclosure pertains to an apparatus for disinfecting an air space that includes a first cartridge and a second cartridge separately connected by a first connecting part, wherein the first cartridge includes first light emitting diodes emitting radiation in a wavelength range of 260 nm to 280 nm outward from the apparatus, and first circuits controlling the first light emitting diodes, and the second cartridge includes second light emitting diodes emitting radiation in a wavelength range of 260 nm to 280 nm outward from the apparatus, and second circuits controlling the second light emitting diodes. The first connecting part includes a fan to pull in ambient air from an area higher than the first cartridge and the second cartridge, circulate the pulled-in air through the first cartridge and the second cartridge, and blow out the air to an area lower than the first cartridge and the second cartridge.

DETAILED DESCRIPTION

Although UVC and its disinfecting properties have been known, many of its applications use mercury lamps. This disclosure pertains to using UVC LEDs for large-area disinfection, adapting UVC LEDs to a realm that has been typically handled by mercury lamps. LEDs offer the advantage of easy power modulation between minimum and maximum output unlike a mercury lamp, which is typically on or off. Power modulation allows on-demand, risk-adjusted disinfection so the user gets an appropriate level of disinfection, as will be explained in detail below. Furthermore, an LED's life is extended by reducing the power. This stands in contrast to a mercury lamp, which degrades each time it is turned on/off. In addition, LEDs are becoming more cost-effective.

A method and apparatus for disinfecting a large area, such as air space, in a nonintrusive yet effective manner is disclosed. Upper room germicidal ultraviolet (UV) apparatus that emits light in the UV-C range (100-290 nm) is disclosed. For example, a wavelength of 260 to 280 nm may be used. In one embodiment, at least 55% of the emitted radiation has a wavelength of 270 nm or less. In another embodiment, at least 90% of the emitted radiation has a wavelength of 280 nm or less. In yet another embodiment, at least 97% of the emitted radiation has a wavelength of 290 nm or less. In some embodiments, all the LEDs in the UR-UVGI apparatus 10 collectively emit in these wavelength ranges. In some embodiments, the UR-UVGI apparatus 10 does not include any LEDs that emit at wavelengths in the visible light range toward the front or the side, such that none of the front-facing LEDs emit in the visible light range. The apparatus may be designed to be installed in the upper part of the room, such as on an upper portion of a wall 7 ft. above the floor, or on the ceiling. UV-C light is generated and aimed at the upper part of the room, above where occupants would be present, to minimize UV exposure to the occupants. The apparatus offers low power use and a high rate of air disinfection while demanding little attention from users.

Although the Upper Room Ultraviolet Germicidal Irradiation (UR-UVGI) apparatus of the disclosure will be described in the text of Upper Room application, this is not a limitation of the inventive concept, and the apparatus may be adapted to other applications and form factors.

Figure 1:
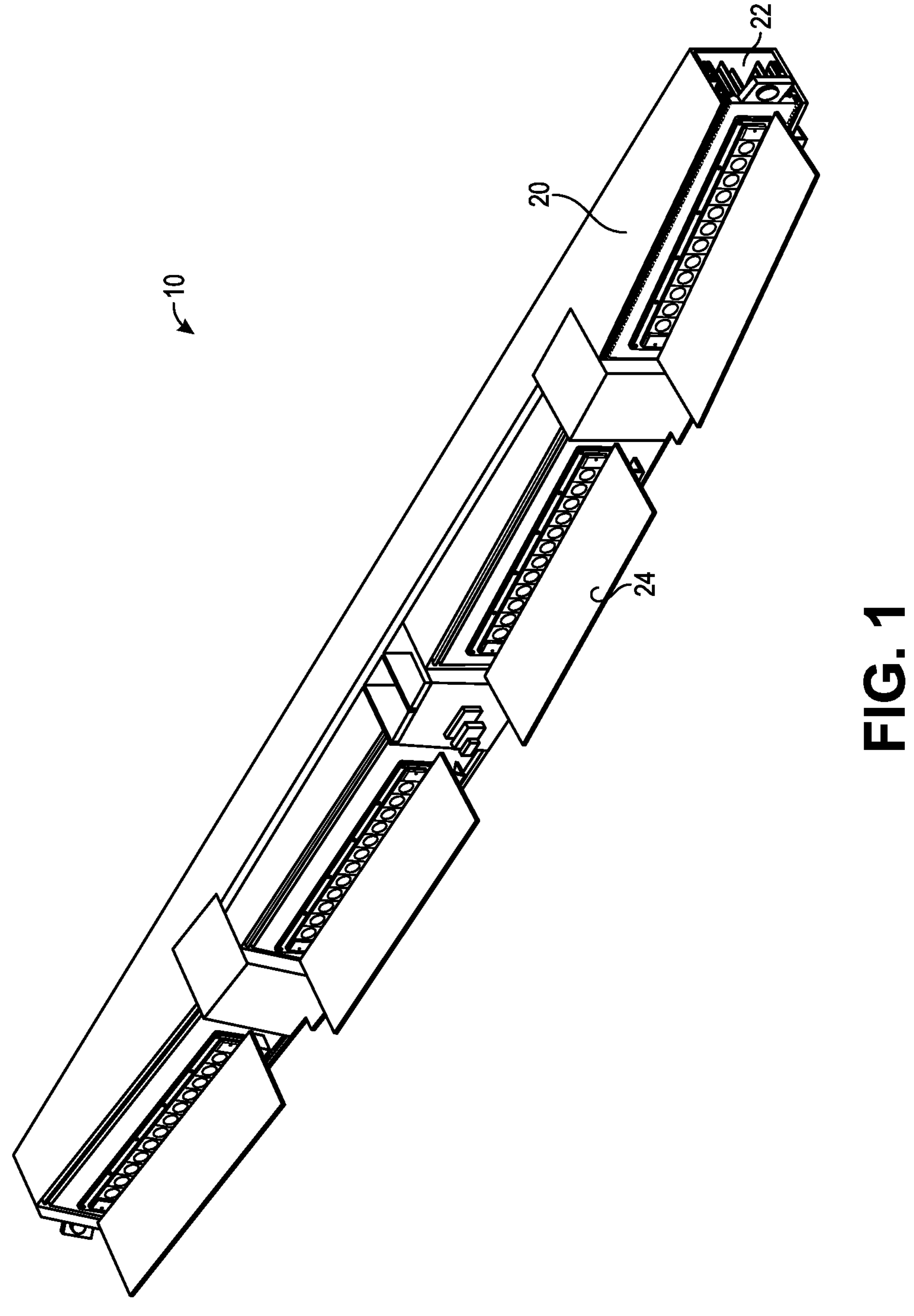
FIG. 1 depicts an Upper Room Ultraviolet Germicidal Irradiation (UR-UVGI) apparatus in accordance with an embodiment of the disclosure.
Figure 2A:
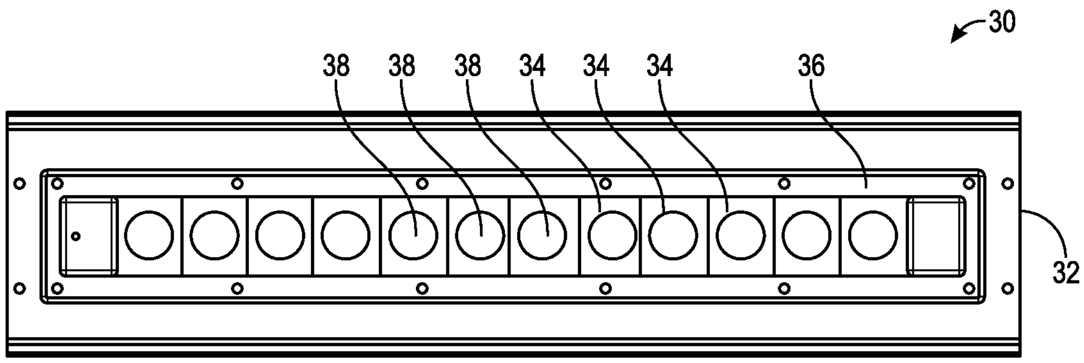
FIG. 2A depicts a front view UR-UVGI cartridge that is inside the housing of the UR-UVGI apparatus, in accordance with an embodiment of the disclosure.
Figure 2B:
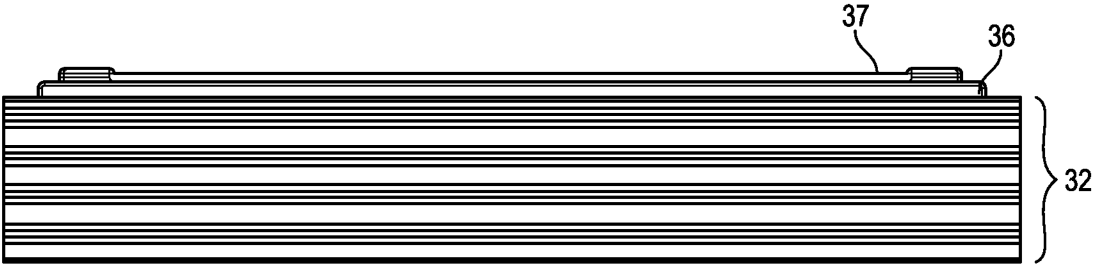
FIG. 2B depicts a side view of the UR-UVGI cartridge depicted in FIG. 2A.
Figure 2C:
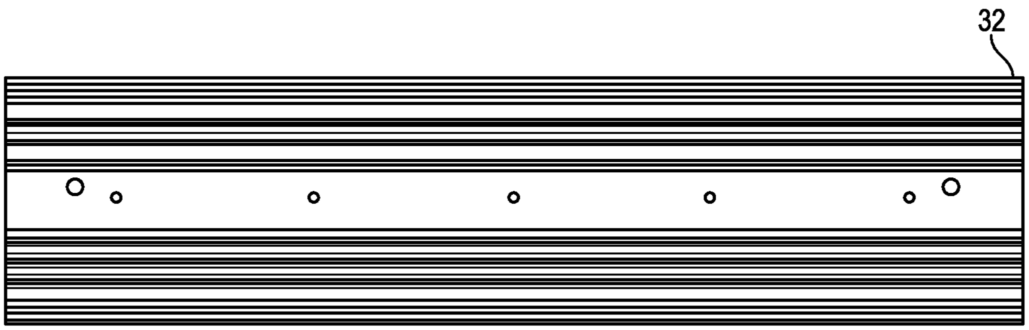
FIG. 2C depicts a back view of the UR-UVGI cartridge depicted in FIG. 2A.
Figure 2D:
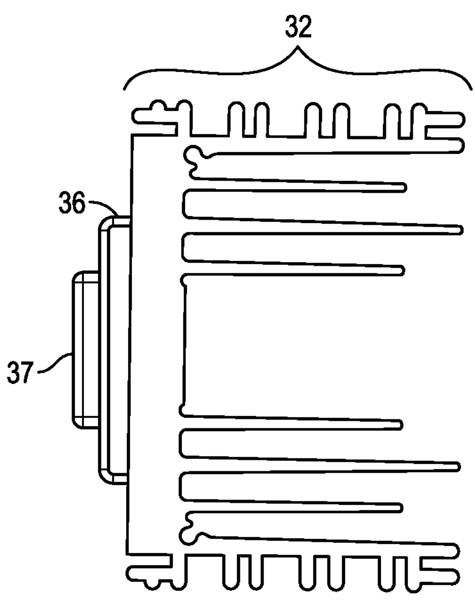
FIG. 2D depicts an end view of the UR-UVGI cartridge depicted in FIG. 2A.
Figure 2E:
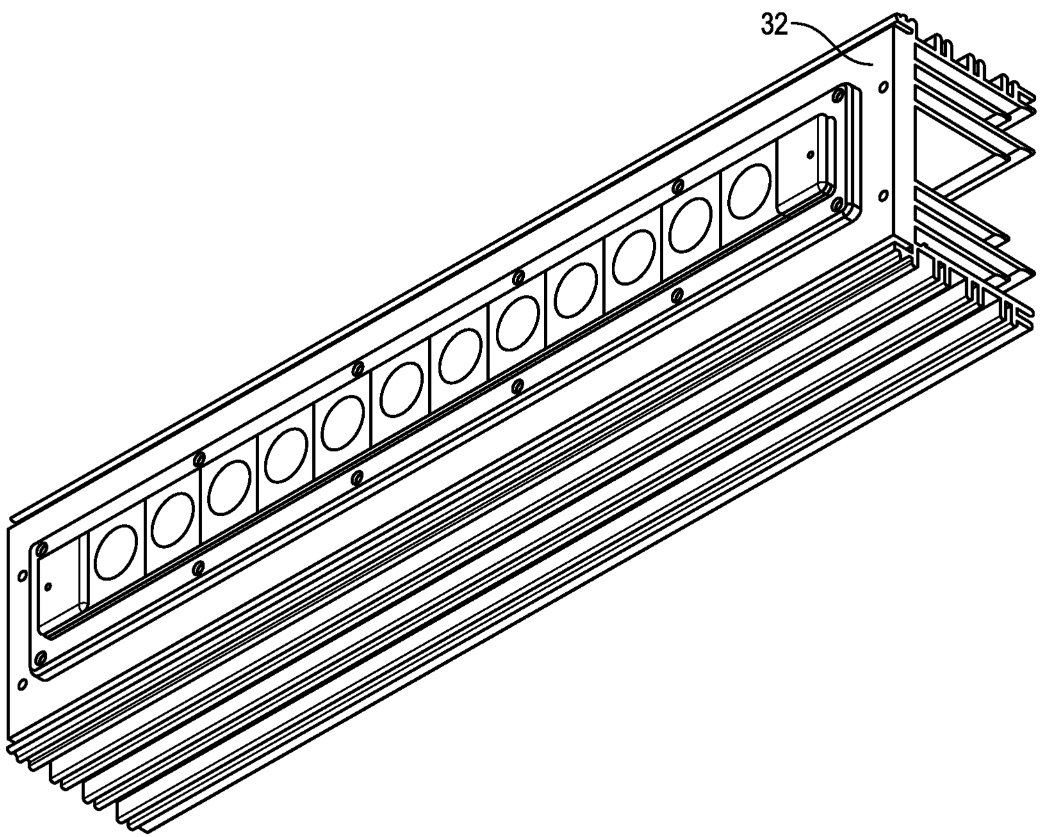
FIG. 2E depicts a perspective view of the UR-UVGI cartridge depicted in FIG. 2A.

FIG. 1 depicts an Upper Room Ultraviolet Germicidal Irradiation (UR-UVGI) apparatus 10 in accordance with an embodiment of the disclosure. The UR-UVGI apparatus 10 includes a housing 20 that has a window 22 allowing UV light to irradiate from the UR-UVGI apparatus 10. As will be described below, the housing 20 has a front surface, a back surface, a top surface, a bottom surface, a first end, and a second end. The housing 20 encloses one or more UR-UVGI cartridges that include UV-C LEDs and provide a mounting or installation mechanism. For example, where the UR-UVGI apparatus 10 has an Upper Room application, the housing 20 includes structures (not shown) that facilitate the UVGI apparatus 10 to be mounted on a wall or a ceiling. The wall mounting mechanism may be on the back surface of the UR-UVGI apparatus 10. The ceiling mounting mechanism may be on the top and/or back surfaces of the UR-UVGI apparatus. The mounting mechanism may include, for example, a hole or an indentation to hang on a nail or protrusion on the wall/ceiling.

In the example of FIG. 1, the back side of the housing 20 that does not include the windows 22 are mounted on the wall, and the front side includes windows 22 that face into the room. In some embodiments, baffles 24 are included under or around the windows 22 to prevent the generated UV radiation from spreading downward toward the room occupants. There are a number of UV wavelength ranges that may be used for disinfection. Where the UV wavelength that is chosen is harmful to humans above a threshold exposure level, baffles 24 may be attached to the housing 20 to reduce or minimize the amount of radiation that is directed below the 7-ft height of the room. Although UVC LEDs are generally directional and may be set up to irradiate the area above the 7-ft. height, the baffle 24 will further reduce any scattered light or light reflecting off the walls from reaching the room occupants. In embodiments where the directionality of radiation is more tightly controlled, baffles may not be necessary at all.

FIGS. 2A, 2B, 2C, 2D, and 2E depict the UR-UVGI cartridges 30 that are disposed inside the housing 20, in accordance with an embodiment of the disclosure. As shown, the particular embodiment of the cartridge 30 that is depicted includes a base 32, LED PCB 36 mounted on the base 32, UVC LEDs 34, and optical elements 38. In the particular embodiment that is shown, the LED 34 and the optical elements 38 are combined or integrated into an LED+ optics array 37. However, this is not a limitation of the inventive concept. The UVC LED array 37 may include a plurality of LEDs 34, for example 12 LEDs 34 arranged in a line. The optical elements 38 may be a silicone UVC lens, another type of lens, or a reflective surface, although this is not a limitation and any known optical element may be selected and/or combined to attain the desired effect and focal length. While the particular embodiment shows there being one optical element 38 for each LED 34, this is not a limitation of the inventive concept and multiple LEDs 34 could share an optical element. The base 32 may be a piece of aluminum backing that allows other components to be mounted thereon. The shape of the base 32 is not limited to what is depicted. The base 32 may function as a heat sink.

Figure 3A:
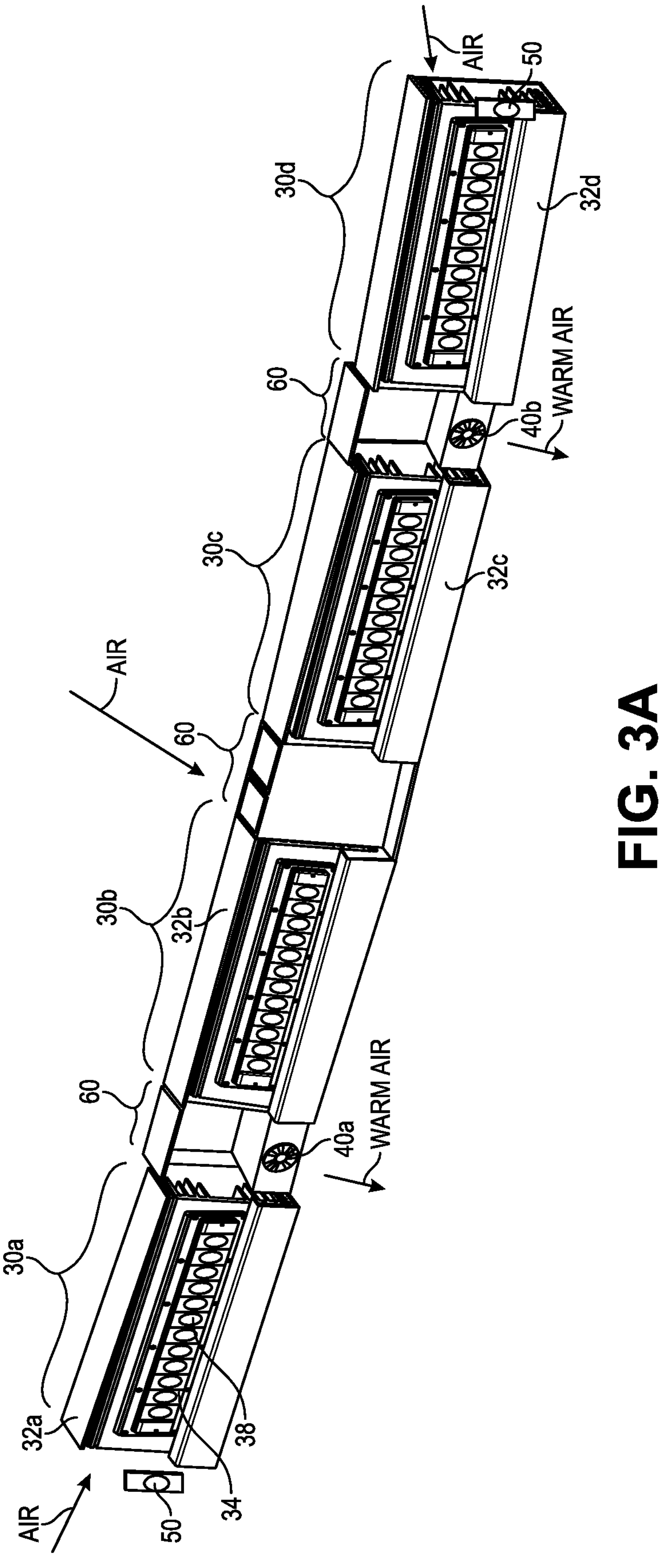
FIG. 3A and FIG. 3B depict four cartridges coupled to one another, in accordance with an embodiment of the disclosure.

The cartridges 30 are modular, and a desired number of cartridges 30 may be interconnected according to the size of the room to be disinfected. FIG. 3A depicts a first cartridge 30*a*, a second cartridge 30*b*, a third cartridge 30*c*, and a fourth cartridge 30*d* (each of which may also be referred to as cartridge 30) coupled to one other, for example through an interlocking mechanism. In the particular embodiment that is illustrated, the base 32*a*/32*b*/32*c*/32*d* has the shape of the base 32 depicted in FIG. 2A. UVC LED 34 and the optical elements 38 are not covered by the base 32, so as to not obstruct the radiation.

In the embodiment of FIG. 3A, there are connection pieces 60 between adjacent cartridges 30. Some connection pieces 60, such as the one between the first cartridge 30*a* and the second cartridge 30*b*, and the one between the third cartridge 30*c* and the fourth cartridge 30*d*, include a fan 40*a*/40*b*. UVC LEDs generate heat, and the UR-UVGI apparatus 10 needs cooling. Where the base 32 is a heat sink, the fans 40*a*, 40*b* direct airflow to transfer heat from the heat sink, and to achieve enhanced mixing between upper and lower layers of air. The connection piece between the second cartridge 30*b* and the third cartridge 30*c* has conduits through which ambient air gets pulled into the UR-UVGI apparatus 10 (as shown by the arrow) when the fans 40*a*, 40*b* are in operation. The air that gets pulled in through the central connection piece 60 flows across the second cartridge 30*b* and the third cartridge 30*c*, transferring heat out of their heat sink/base 32*b*, 32*c*. The warmed-up air gets blown out in a downward direction by the fans 40*a*, 40*b*. Similarly, ambient air gets pulled in from the two ends (see the arrows), flows across the first cartridge 30*a* and the fourth cartridge 30*d* to cool down the heat sink/base 32*a*, 32*d*, and gets blown out in a downward direction by the fans 40*a*, 40*b*. In some embodiments, the fans 40*a*, 40*b* operate to pull in and blow out ambient air only when the LEDs are actively emitting radiation, to conserve power.

Although not explicitly shown in the figures, the cartridges 30 include thermocouples for monitoring the temperature of the cartridges 30 and the surrounding elements to maintain optical operating conditions for the UR-UVGI apparatus 10. In one embodiment, the circuits may control the speed of the fans 40*a*/40*b* to pull in the ambient air faster to cool the LEDs 34 more effectively in response to the thermocouple detecting a highly-heated LEDs 34. The exact adjustment of the fan speed takes into account not just the temperature of the LEDs 34 but also the ambient temperature, which affects the temperature of the ambient air that is circulated in the cartridge 30. The cooler the ambient air is, the more effective it will be in bringing down the temperature of heated LEDs. Once the LEDs are back to a normal temperature range, the fans 40*a*/40*b* may also return to achieve a "normal" level of heat transfer out of the LEDs. Maintaining the LEDs at ehri optimal temperature ensures that the LEDs will last through their intended lifespan.

The cartridges 30 include EEPROMs integrated to hold data about the LEDs 34, such as their usage and lifespan. In some embodiments, a "warning" may be generated in the form of an audio and/or visual alert when LEDs are close to reaching the end of their lifespan. Furthermore, data stored in the EEPROM can be used to inform a technician if a counterfeit cartridge or part was used for the UR-UVGI apparatus 10.

In the embodiment of FIG. 3A, ambient air is pulled in from an upper portion and side portions and warm air is blown out downward to enhance convective mixing of air in the room. Although the housing 20 is not shown in FIG. 3A, the housing 20 is designed with openings at the right places to allow the flow of air in the manner described. The pulled in air travels primarily through the cavity between the base 32 and the inner surface of the back of the housing 20.

Figure 3B:
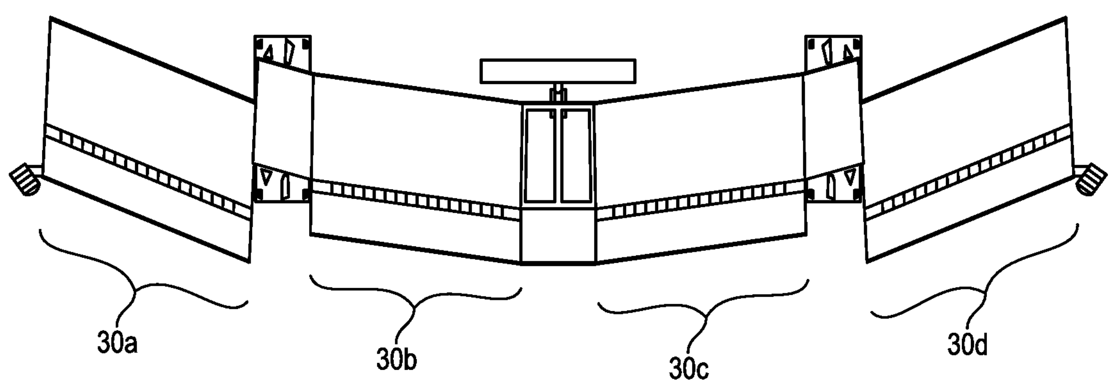

In the embodiment of FIG. 3A, the first cartridge 30*a* and the fourth cartridge 30*d* are connected to the rest of the pieces in a staggered manner. FIG. 3B, which depicts a top view of the device of FIG. 3A, shows the staggered arrangement. In the embodiment of FIG. 3A and FIG. 3B, the cartridges 30*a*, 30*b*, 30*c*, 30*d* are arranged angled about 3°-8°, for example about 5°, to optimize coverage area and radiation intensity. As lining up the cartridges 30*a*, 30*b*, 30*c*, 30*d* at the chosen angle may result in the UR-UVGI apparatus 10 being deeper and bulkier, select cartridges (in this case the first cartridge 30*a* and the fourth cartridge 30*b*) are staggered to reduce the overall depth of the apparatus 10.

The window 22 may be the only transparent or transmissive portion of the housing 20, helping direct the radiation toward the desired space. In some embodiments, the window 22 is an opening in the front surface of the UR-UVGI apparatus 10. Although the LEDs of the LED array 34 may be the same, their positions with respect to the window vary because of the cartridges 30 being positioned at an angle or being staggered, as described above in reference to FIG. 3B. For example, the LED of the first cartridge 30*a* that is closest to the end is closer to the wall than the LED in the same LED array 34. To even out and optimize the radiation intensity received by the space, the shape of the window may not be symmetric along the lengthwise direction. For example, as depicted in FIG. 5B, the window may get wider as it gets closer to the end (farther from the center), so that the LEDs that are farther back (closer to the wall) get a bigger window than the LEDs that are positioned closer to the center of the room.

Figure 4A:
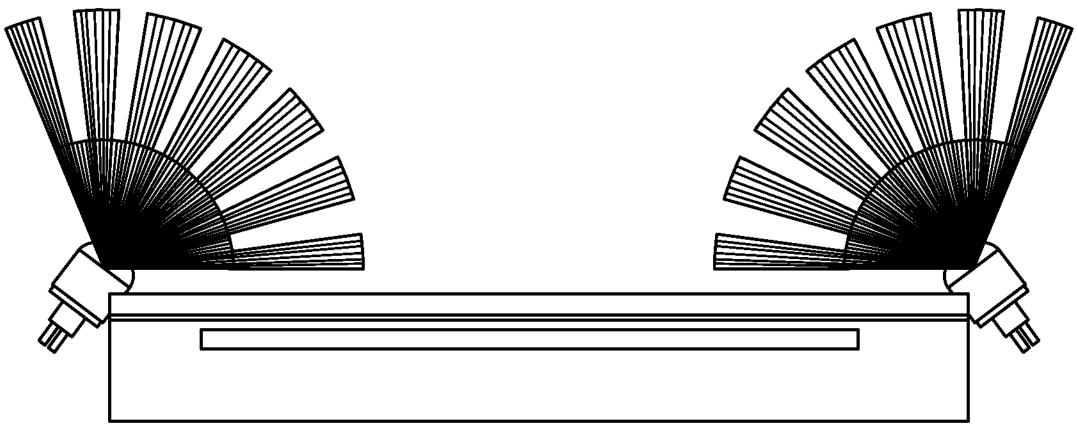
FIG. 4A depicts the sensed area monitored by the PIR sensors of the UR-UVGI apparatus, in accordance with an embodiment of the disclosure.

The UR-UVGI apparatus 10 includes upper room presence detection sensors 50, which may be but are not limited to PIR sensors 50. In the embodiment of FIG. 3A, the upper room PIR sensors 50 may be positioned at the ends of the UR-UVGI apparatus 10, facing horizontally. The UVC LEDs 34 may emit disinfection wavelengths that are not safe for humans and animals to be exposed to over a threshold level. The PIR sensors 50 allow detection of motion, which indicates whether the space/room is occupied so the UR-UVGI apparatus 10 may adjust its radiation intensity and on/off status. FIG. 4A depicts the sensed area monitored by the upper room PIR sensors 50 at the ends. The upper room PIR sensors may be shielded so they primarily monitor the upper room area (e.g., above 7 ft. height). The UR-UVGI apparatus 10 may include a microprocessor that is programed to activate the UVC LED array 34 when no motion is detected for a given amount of time.

Figure 4B:
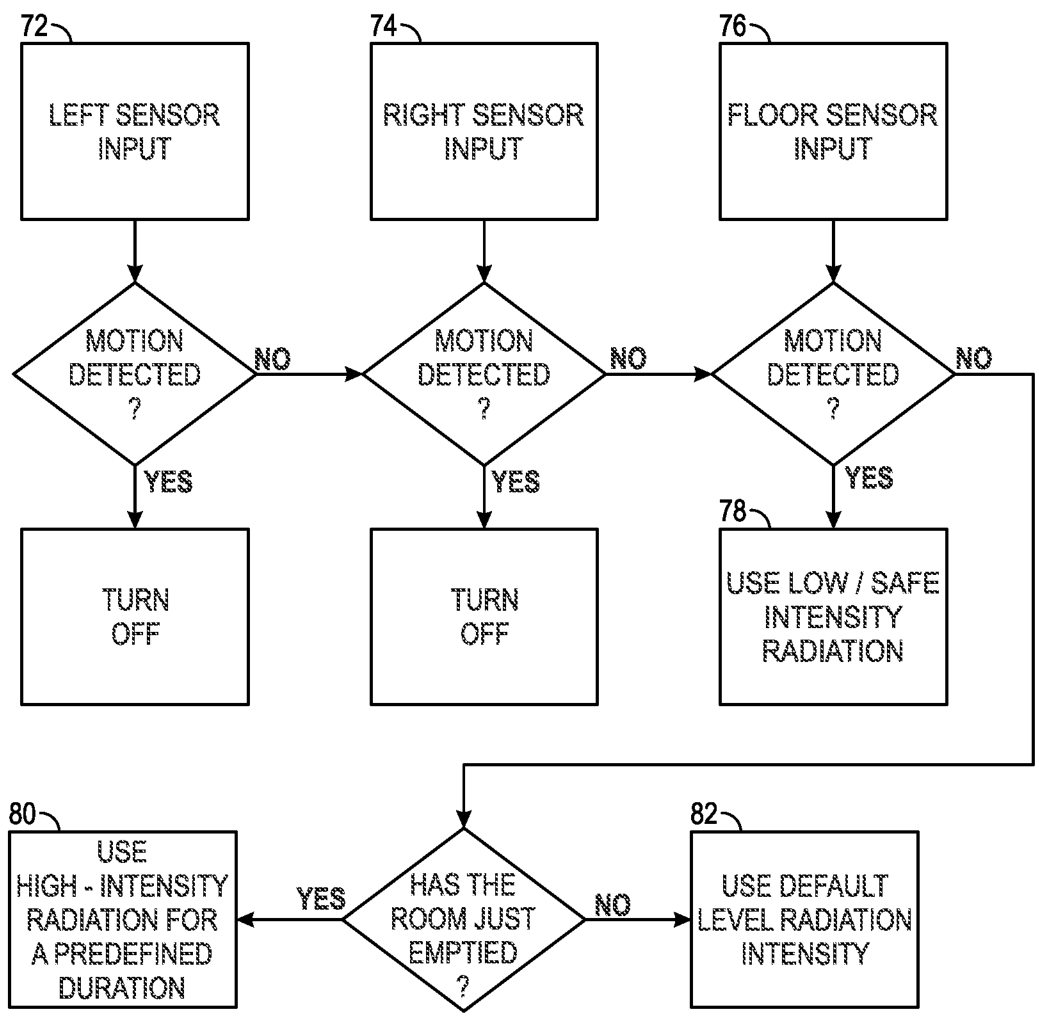
FIG. 4B depicts a dynamic intensity modulation process that may be used by the UR-UVGI apparatus in accordance with an embodiment of the disclosure.

In addition to the upper room PIR sensors 50 at the two ends of the UR-UVGI apparatus 10, an additional PIR sensor 50 may be positioned to monitor the floor level space and detect the presence of occupants. With the upper room PIR sensor 50 and the floor level PIR sensor 50, the UR-UVGI apparatus 10 may adjust the intensity of radiation as well as turn itself on and off according to sensor readings. FIG. 4B depicts a dynamic intensity modulation process 70 that may be used by the UR-UVGI apparatus 10 in accordance with an embodiment. In this embodiment, the left sensor and the right sensor inputs 72, 74 (inputs from the upper room PIR sensors 50) are continually monitored (e.g., every second) to see if any motion is detected in the upper room area, or in front of the upper room PIR sensors 50. When motion is detected in the disinfecting area by the upper room PIR sensor 50, the UR-UVGI apparatus 10 automatically shuts itself off. This way, an electrician who climbs up a ladder to service a light fixture on the ceiling will not be exposed to a high level of UV radiation because the upper room PIR sensor 50 will detect his motion.

In one embodiment, the UR-UVGI apparatus 10 includes presence sensors 50 for multiple detection zones, including disinfection and occupied zones. The circuits in the UR-UVGI apparatus 10 may communicate with (for example, using Bluetooth or some other type of wired or wireless communication protocol) presence sensors located in different parts of a room, physically separated from the body of the apparatus 10. This way, the UR-UVGI apparatus 10 is able to detect the presence of people over a larger area with higher accuracy.

The UR-UVGI apparatus 10 may include a floor level PIR sensor 50 that monitors motion at the floor level of the space. In one embodiment, the floor level PIR sensor is located on the bottom surface of the apparatus 10 and faces downward instead of horizontally. When the floor level sensor 50 detects motion 76, it usually indicates the presence of a person or animal in the room. When motion is detected by the floor level sensor 50, a low/safe intensity is used for the upper room so that the air in the room is safely disinfected 78 with people present. When no motion is detected and the room just emptied (e.g., motion was continually detected for the last 30 minutes but not for the last minute), the UVC LEDs may use a high-intensity radiation for a predefined duration (e.g., 10 minutes) 80 to disinfect the room. If the floor sensor does not detect any motion and there has been no motion detected for a while, indicating that the room has been empty for at least a predetermined length of time, a low, default level radiation may be used to maintain the desired disinfection level of the room 82. This dynamic intensity modulation process 70 maintains a low level of bacteria, virus, and pathogens in the room while protecting room occupants from a high level of UV exposure. The process 70 may be partly or entirely run by a microprocessor on the PCB 36, optionally communicating with a cloud server.

In one embodiment, all the cartridges 30 in a UR-UVGI apparatus 10 may be identical. The cartridges may be coupled and separated from each other using an interlocking mechanism, allowing each cartridge 30 to be replaced independently of the other cartridges 30. Furthermore, the LED array 37 may be unscrewed from the LED PCB 36 and be replaced if one or more LEDs burn out. This modular nature of the LED array 37 and/or LED cartridges 30 is advantageous because while the LEDs have a general life span of X hours (e.g., 2000 hours), some LEDs will burn out before others.

The number of cartridges 30 in a UR-UVGI apparatus 10 is adjustable. For example, if four cartridges 30 are designed to disinfect a 500-sq. ft. space, two cartridges 30 may be removed to disinfect a smaller (e.g., 250-sq. ft.) space. Also, by replacing less powerful LEDs with more powerful LEDs, four cartridges 30 may achieve the same level of disinfection for a space larger than 500 sq. ft. Each cartridge 30 may include an EEPROM that indicates authenticity and proper match to the UVGI apparatus 10, making it difficult to install an incorrect cartridge that does not optimize the unit's performance.

The directionality of UVC LEDs, the baffle, the housing 20, the fans 40*a*, 40*b*, and the dynamic intensity modulation process 70 work together to minimize occupants' exposure to UVC radiation without compromising disinfection efficiency.

Figure 5A:
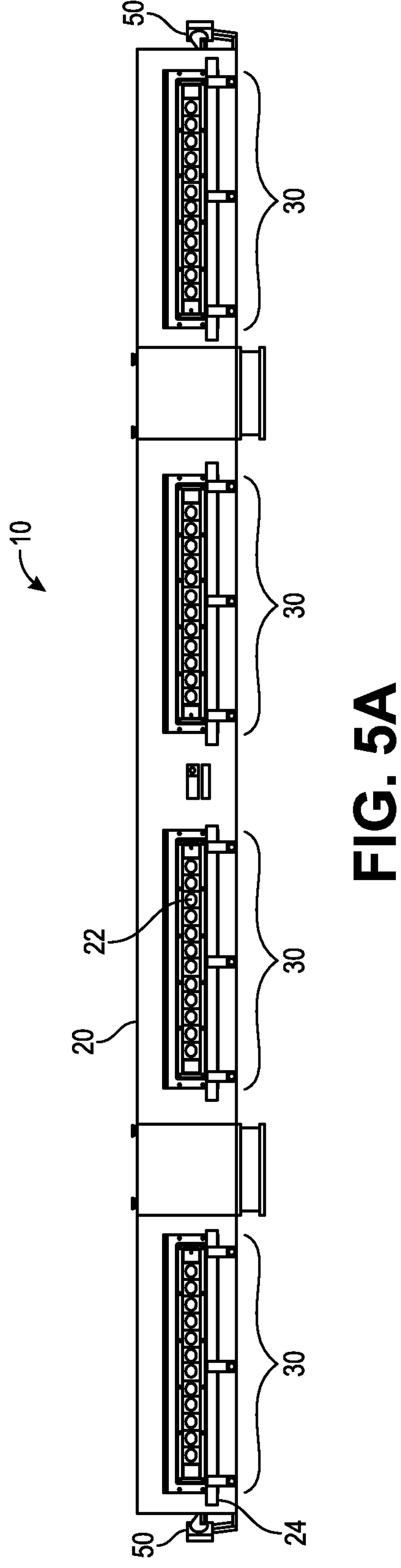
FIG. 5A depicts a front view of the UR-UVGI apparatus with housing in accordance with an embodiment of the disclosure.
Figure 5B:
FIG. 5B depicts a top view of the UR-UVGI apparatus with housing, in accordance with the embodiment of FIG. 5A.
Figure 5B:
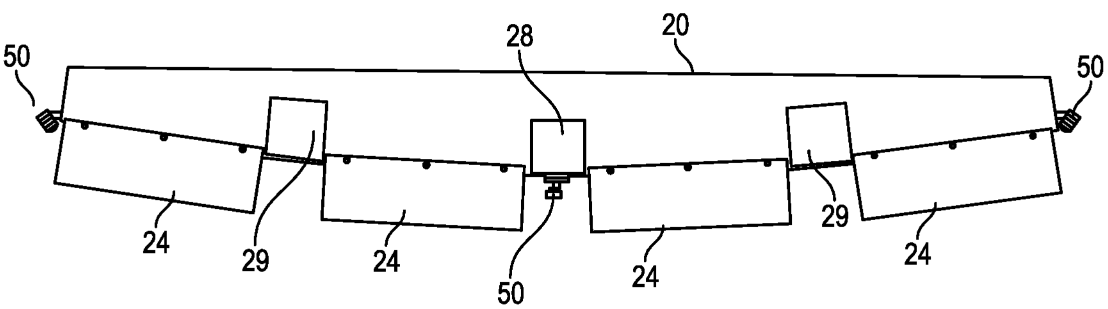

FIG. 5A depicts a front view of the UR-UVGI apparatus 10 including the housing 20, in accordance with an embodiment. As shown, the window 22 allow irradiation of the space in front of the apparatus 10. The baffles 24 minimize the amount of radiation that might spread to a lower area of the space. The baffles 24 not only shadow stray light from the LEDs but also helps direct the disinfection zone presence sensors 50 by shielding the presence sensors 50. The presence sensors being shielded by the baffles helps avoid "false positives" that might compromise the effectiveness of the apparatus 10. In the embodiment of FIG. 5A, there is a separate baffle 24 for each window 22.

Figure 5C:
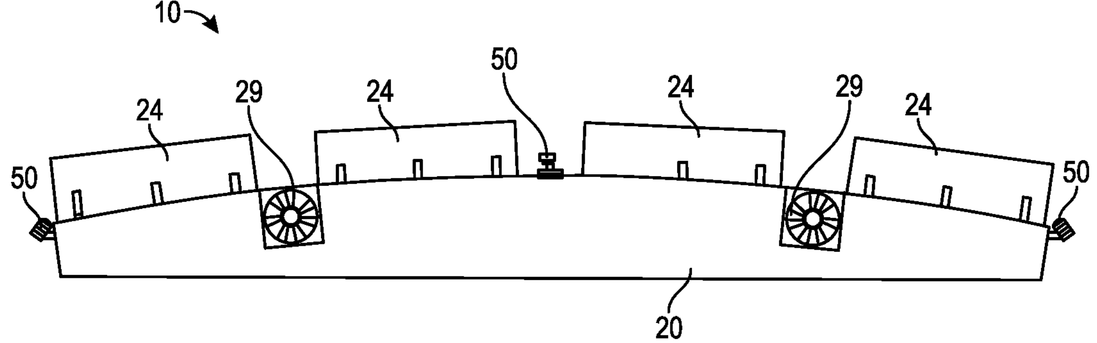
FIG. 5C depicts a bottom view of the UR-UVGI apparatus with housing, in accordance with the embodiment of FIG. 5A.
Figure 5D:
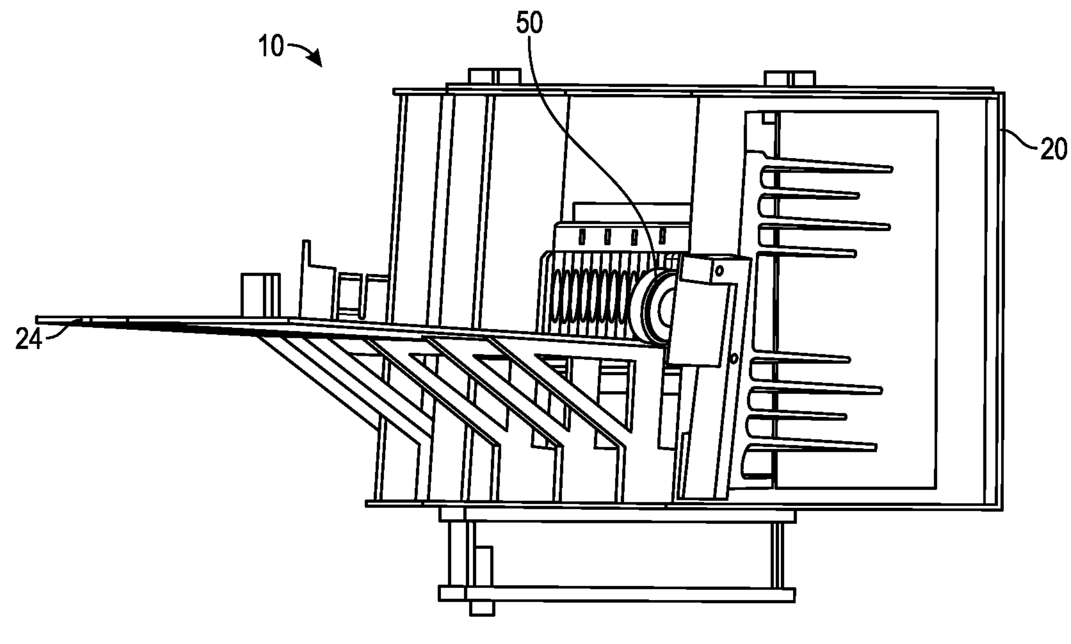
FIG. 5D depicts a side view of the UR-UVGI apparatus with housing, in accordance with an embodiment.

FIG. 5B depicts a top view of the UR-UVGI apparatus 10 including the housing 20 with baffles 24. The floor motion sensor 50 is positioned at the lengthwise center of the apparatus 10, and there are holes 28 through which ambient air gets pulled into the apparatus 10. There are also fan compartments 29 located in the apparatus 10 between baffles 24. FIG. 5C depicts a bottom view of the UVGI apparatus 10 in accordance with an embodiment. Although not explicitly shown, the fan compartments 29 have holes visible from the bottom to blow out warmed air. FIG. 5D depicts a side view of the UR-UVGI apparatus 10 in accordance with an embodiment. Pulling in the ambient air from the top, passing it through the apparatus 10 to place it in contact with the cartridge 32, and blowing the warmed air out through the bottom helps achieve effective air circulation in the space.

Figure 6A:
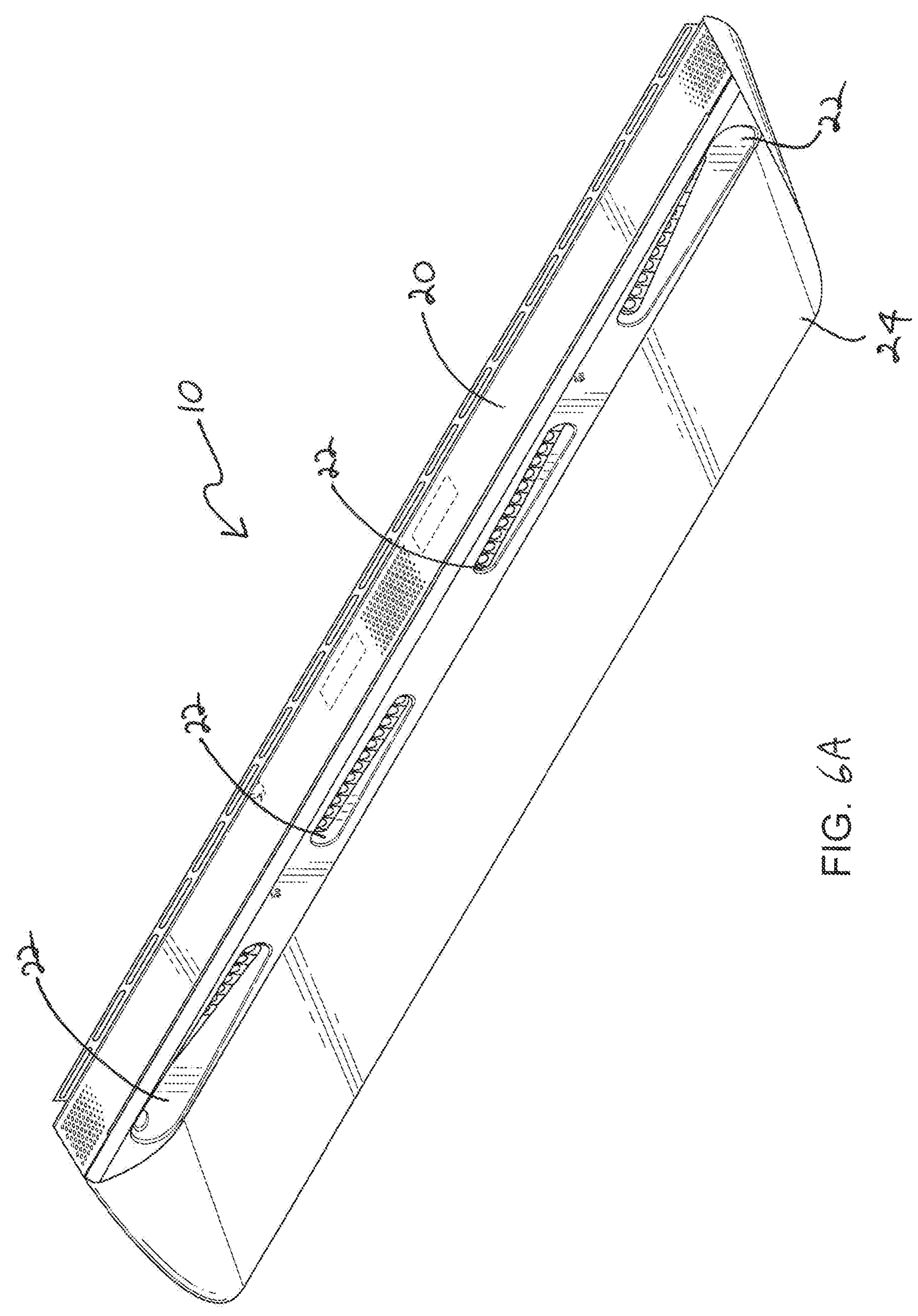
FIG. 6A depicts a perspective view of the UR-UVGI apparatus in accordance with another embodiment of the disclosure.
Figure 6B:
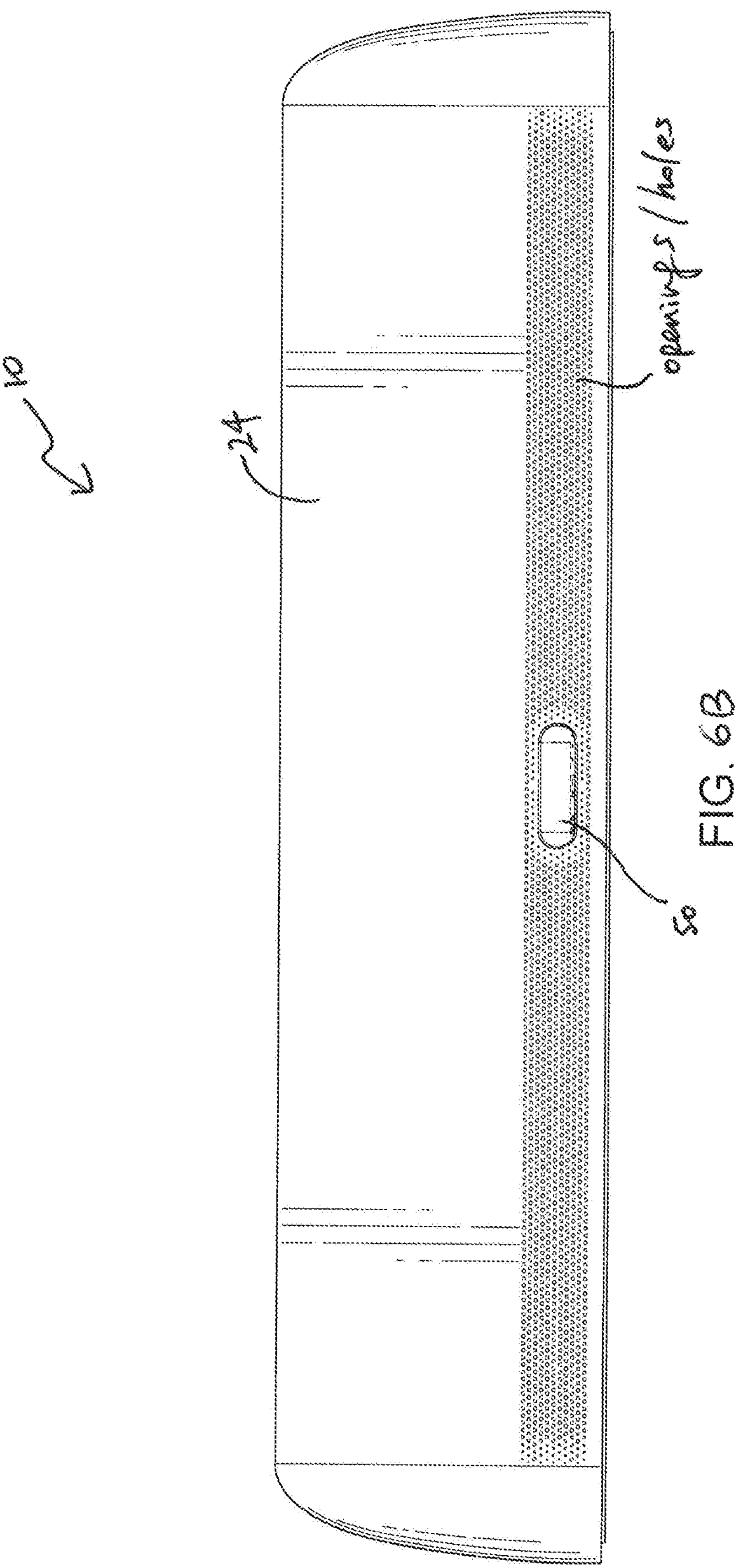
FIG. 6B depicts a bottom view of the UR-UVGI apparatus including a housing with a baffle, in accordance with the embodiment of FIG. 6A.
Figure 6C:
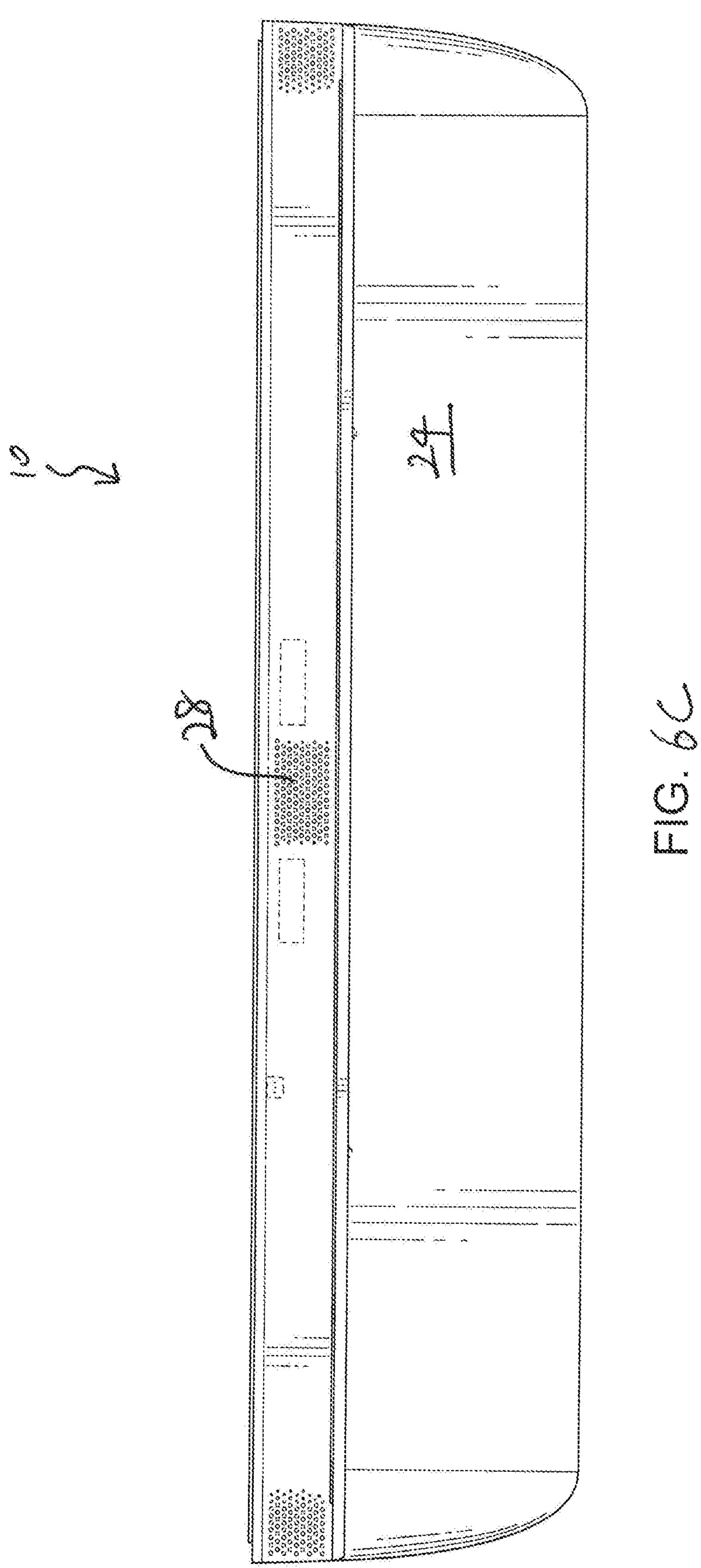
FIG. 6C depicts a top view of the UR-UVGI apparatus in accordance with the embodiment of FIG. 6A.
Figure 6D:
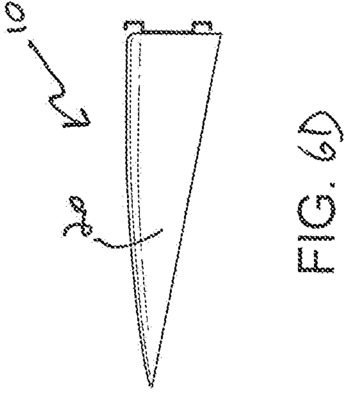
FIG. 6D depicts a side view of the UR-UVGI apparatus in accordance with the embodiment of FIG. 6A.

FIG. 6A depicts a perspective view of the UR-UVGI apparatus 10 including the housing 20, in accordance with another embodiment. In this embodiment, the housing 20 has windows 22 that may be openings or windows made of a transparent material. In the embodiment of FIG. 6A, the windows 22 are shaped so that the openings widen with distance from the center of the apparatus 10. Each window 22 may be shaped such that it gets wider as it extends away from the center. In the embodiment of FIG. 6A, one long baffle 24 is shared by multiple windows 22. FIG. 6B depicts a bottom view of the UR-UVGI apparatus 10. In this shared-baffle embodiment, the floor motion sensor 50 is seen through the bottom surface. The bottom surface has openings/holes through which warmed air is blown out, as described above. FIG. 6C depicts a top view of the UR-UVGI apparatus 10 showing holes 28 through which ambient air can get pulled into the apparatus 10. FIG. 6D depicts a side view of the UR-UVI apparatus 10 in accordance with an embodiment. In this embodiment, the upper room PIR sensors 50 are enclosed by the housing 20 such that they are not visible from the side.

In the embodiments of FIG. 5A and FIG. 6A, there may be a magnetic sensor that detects if the UR-UVGI apparatus 10 is in "service mode." The baffle may be "down" in service mode. When the circuits recognize that the apparatus 10 is in service mode, the LEDs are shut off to ensure that the maintenance person is not exposed to harmful radiation.

Furthermore, the UR-UVGI apparatus 10 may include a visible light LED on the bottom surface facing the floor that displays the status of the device operation, to communicate the operation status to occupants of the room. In one embodiment, the visible light LED being white indicates that the apparatus is in standby mode, pulsing blue light indicates that the apparatus 10 is in disinfecting mode, and pulsing red light indicates that disinfection zone is intruded. This visible light LED on the bottom surface may be replaced or supplemented by other means of communicating the operational status to room occupants, such as a display, a graphical display, and/or an alpha display as well as an audio signal generator.

Figure 7:
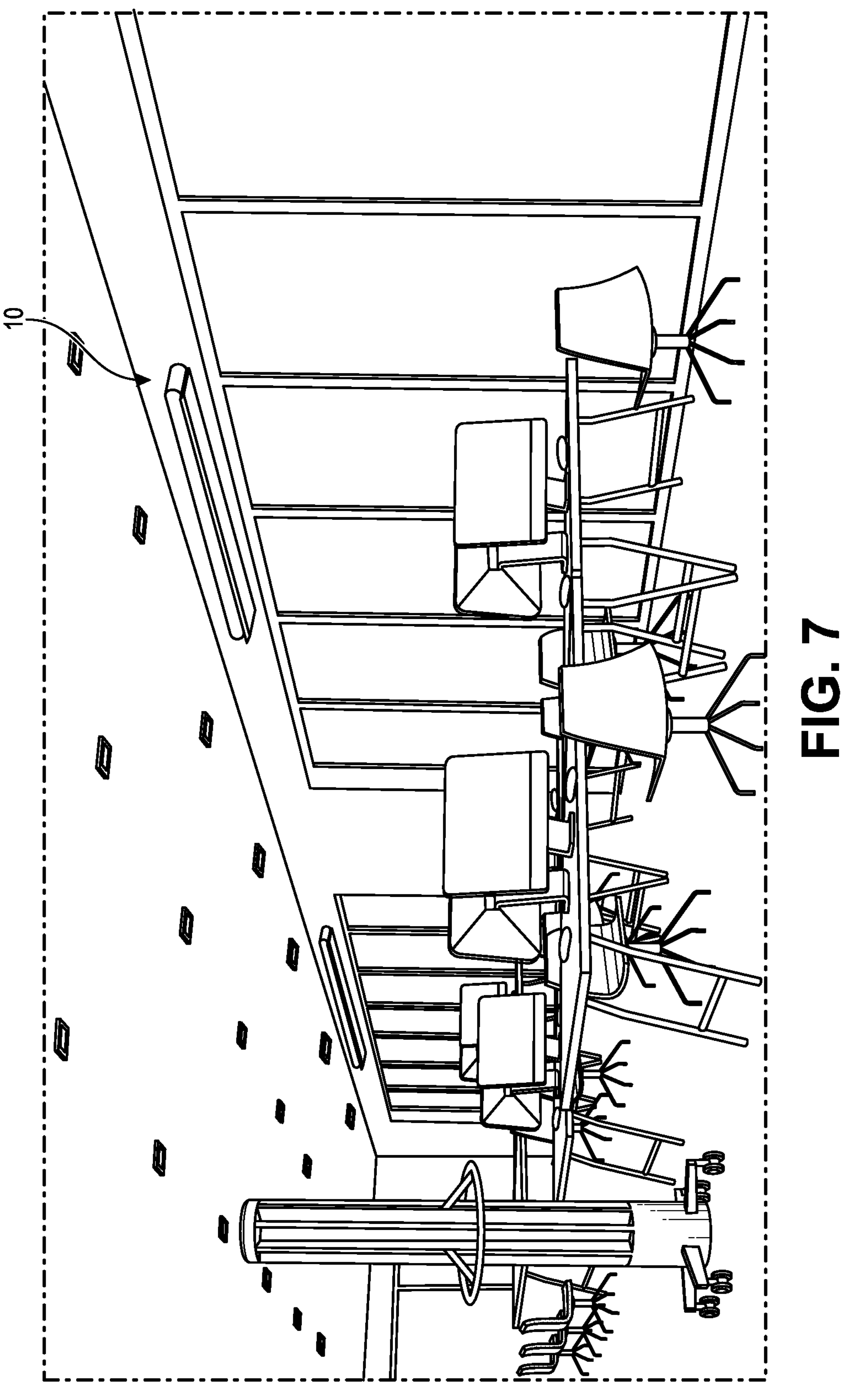
FIG. 7 depicts the UR-UVGI apparatus installed on a wall in accordance with an embodiment of the disclosure.

FIG. 7 depicts the UVGI apparatus 10 installed on the upper wall of a room, in accordance with an embodiment.

In some embodiments, the UR-UVGI apparatus 10 may include a gyroscope to detect that the apparatus has been installed at the correct angle. Due to the directionality of the UVC LEDs, correct installation helps minimize UV exposure to room occupants. The accelerometer also helps detect if the UR-UVGI apparatus 10 has partially or completely fallen off its proper position. With the accelerometer, if the apparatus is not in its proper position, the device may automatically shut off for safety.

While the embodiments are described in terms of a method or technique, it should be understood that the disclosure may also cover an article of manufacture that includes a non-transitory computer readable medium on which computer-readable instructions for carrying out embodiments of the method are stored. The computer readable medium may include, for example, semiconductor, magnetic, opto-magnetic, optical, or other forms of computer readable medium for storing computer readable code. Further, the disclosure may also cover apparatuses for practicing embodiments of the inventive concept disclosed herein. Such apparatus may include circuits, dedicated and/or programmable, to carry out operations pertaining to embodiments.

Examples of such apparatus include a general purpose computer and/or a dedicated computing device when appropriately programmed and may include a combination of a computer/computing device and dedicated/programmable hardware circuits (such as electrical, mechanical, and/or optical circuits) adapted for the various operations pertaining to the embodiments.

It should be understood that the inventive concept can be practiced with modification and alteration within the spirit and scope of the disclosure. The description is not intended to be exhaustive or to limit the inventive concept to the precise form disclosed.

What is claimed is:

1. An apparatus for disinfecting an air space, comprising:

a housing having a front surface, a back surface, a top surface, a bottom surface, a first end, and a second end;

a wall-mounting mechanism on the back surface to secure the apparatus to a wall;

a light emitting diode on a base inside the housing positioned to emit radiation toward a disinfection space in front of the front surface, wherein at least 90% of the radiation has a wavelength less than 280 nm;

a cavity between the base and the back surface guiding air flow between the first end and the second end;

one or more lower baffles, each lower baffle extending from a lower portion of the front surface and below at least one light emitting diode, wherein the one or more lower baffles define (1) the disinfection space that radiation is emitted toward and (2) an occupancy space below the disinfection space, the one or more lower baffles configured to limit emitted radiation in the occupancy space;

at least one first occupancy sensor configured to sense an occupancy in the disinfection space;

at least one second occupancy sensor configured to sense an occupancy in the occupancy space; and circuits inside the housing controlling the light emitting diode to emit radiation at different intensity levels including zero.

2. The apparatus of claim 1, wherein the circuits are coupled to the base.

3. The apparatus of claim 1, wherein the light emitting diode is on a front portion of the base, and the base comprises an upper portion and a bottom portion that form a space for airflow.

4. The apparatus of claim 1 further comprising optical elements positioned on the front surface of the light emitting diode.

5. The apparatus of claim 1, further comprising a ceiling-mounting mechanism on the top surface for attaching the apparatus to a ceiling.

6. The apparatus of claim 1, wherein the light emitting diode is one light emitting diode of a plurality of light emitting diodes arranged in a row inside the housing, and the plurality of light emitting diodes emit radiation through a window on the front surface of the housing.

7. The apparatus of claim 6, wherein the window is an opening.

8. The apparatus of claim 6, wherein all the light emitting diodes in the apparatus emit radiation that is at least 90% in a wavelength range less than 280 nm.

9. The apparatus of claim 6, wherein the plurality of light emitting diodes are arranged in a line that forms an angle of about 3° to about 8° with respect to the back of the housing.

10. The apparatus of claim 1, wherein the apparatus does not have any baffles that limit emitted radiation above the occupancy zone.

11. The apparatus of claim 1, wherein at least one of the first or second occupancy sensors is attached to at least one of the first end or the second end.

12. The apparatus of claim 1, wherein the circuits are configured to turn off the light emitting diode when the first occupancy sensor detects an occupancy in the disinfection space.

13. The apparatus of claim 1, wherein the circuits are configured to power on the light emitting diode when the second occupancy sensor detects an occupancy in the occupancy space and the first occupancy sensor does not detect an occupancy in the disinfection space.

14. The apparatus of claim 13, wherein the circuits are further configured to set the light emitting diode to a default level of emission when the second occupancy sensor does not detect an occupancy in the occupancy space and the first occupancy sensor does not detect an occupancy in the disinfection space.

15. The apparatus of claim 13, wherein the circuits are further configured to cause the light emitting diode to emit high-intensity radiation when the first occupancy sensor does not detect an occupancy in the disinfection space and the second occupancy sensors detects a change in the occupancy space from occupied to unoccupied.

* * * * *